(12) United States Patent
Candau

(10) Patent No.: US 6,214,324 B1
(45) Date of Patent: Apr. 10, 2001

(54) PHOTOPROTECTIVE/COSMETIC COMPOSITIONS COMPRISING BENZOTRIAZOLE AND BENZOAZOLYL/ BENZODIAZOLYL SUNSCREENS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/503,941

(22) Filed: Feb. 14, 2000

(30) Foreign Application Priority Data

Feb. 12, 1999 (FR) .................................................. 99 01728

(51) Int. Cl.⁷ .............................. A61K 7/42; A61K 7/44; A61K 7/00
(52) U.S. Cl. .............................. 424/59; 424/60; 424/400; 424/401
(58) Field of Search ................................ 424/59, 60, 400, 424/401

(56) References Cited

FOREIGN PATENT DOCUMENTS

| 0 669 232 A1 | 8/1995 | (EP) . |
| 0 843 995 A2 | 5/1998 | (EP) . |
| 0 860 165 A1 | 8/1998 | (EP) . |
| 0 893 119 A1 | 1/1999 | (EP) . |

*Primary Examiner*—Shelley A. Dodson
(74) *Attorney, Agent, or Firm*—Burns, Doane, Swecker & Mathis, L.L.P.

(57) ABSTRACT

Topically applicable sunscreen/cosmetic compositions well suited for the synergistically enhanced photoprotection of human skin and/or hair against the damaging effects of UV-irradiation, particularly solar radiation, comprise synergistically UV-photoprotecting effective amounts of each of (a) at least one benzotriazole compound, and (b) at least one compound containing at least two benzoazolyl groups and/or at least one benzodiazolyl group, formulated into a topically applicable, cosmetically acceptable vehicle, diluent or carrier therefore.

34 Claims, No Drawings

PHOTOPROTECTIVE/COSMETIC COMPOSITIONS COMPRISING BENZOTRIAZOLE AND BENZOAZOLYL/BENZODIAZOLYL SUNSCREENS

CROSS-REFERENCE TO PRIORITY APPLICATION

This application claims priority under 35 U.S.C. §119 of FR-99/01728, filed Feb. 12, 1999, hereby expressly incorporated by reference.

CROSS-REFERENCE TO COMPANION APPLICATIONS

Copending applications Ser. No. 09/503,169, Ser. No. 09/503,943, Ser. No. 08/503,944, Ser. No. 09/503,940, and Ser. No. 09/503,940, each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or hair against ultraviolet radiation (such compositions hereinafter simply designated "antisun," "sunscreen" or "photoprotective" compositions) and to the use of same for the cosmetic applications indicated above.

This invention more especially relates to the aforesaid sunscreen/cosmetic compositions comprising, formulated into a cosmetically acceptable vehicle, diluent or carrier thereof, a binary combination of (a) at least one specific benzotriazole compound, as a first screening agent, and (b) as a second screening agent, at least one compound containing at least two benzoazolyl groups and/or at least one compound containing at least one benzodiazolyl group, said first and second screening agents being present in proportions suitable for eliciting a synergistic effect with regard to the sun protection factors conferred.

2. Description of the Prior Art

It is known to this art that light radiation of wavelengths of from 280 nm to 400 nm promotes tanning of the human epidermis and that irradiation with wavelengths of from 280 to 320 nm, i.e., UV-B irradiation, causes erythemas and skin burns which may be harmful to the development of natural tanning; this UV-B radiation must therefore be screened from the skin.

It is also known to this art that UV-A radiation, with wavelengths of from 320 to 400 nm, which causes tanning of the skin, also adversely affects it, in particular in the case of sensitive skin or of skin continually exposed to solar radiation. UV-A rays cause, in particular, a loss in the elasticity of the skin and the appearance of wrinkles, resulting in premature aging. Such irradiation promotes the triggering of the erythemal reaction or accentuates this reaction in certain individuals and can even be the cause of phototoxic or photoallergic reactions. It is therefore desirable to also screen out UV-A radiation.

A wide variety of cosmetic compositions for the photoprotection (UV-A and/or UV-B) of the skin are known to this art.

These photoprotective/sunscreen compositions are typically emulsions of oil-in-water type (namely, a cosmetically acceptable vehicle, diluent or carrier comprising a continuous aqueous dispersing phase and a non-continuous oily dispersed phase) which comprises, at various concentrations, one or more conventional lipophilic and/or hydrophilic organic screening agents capable of selectively absorbing harmful UV radiation, these screening agents (and their amounts) being selected according to the desired protection factor (the protection factor (PF) being expressed mathematically by the ratio of the irradiation time required to attain the erythemogenic threshold with the UV screening agent to the time required to attain the erythemogenic threshold without UV screening agent).

SUMMARY OF THE INVENTION

It has now surprisingly and unexpectedly been determined that the binary combination of two specific sunscreens already per se known to this art provides synergistically active sunscreen/antisun compositions exhibiting markedly improved protection factors, protection factors which are much higher than those which can be obtained either with one or the other of the screening agents used alone.

Briefly, the present invention features novel cosmetic compositions, in particular photoprotective/sunscreen compositions, comprising, in a cosmetically acceptable vehicle, diluent or carrier (a) a specific benzotriazole compound, as a first screening agent, and (b) at least one compound containing at least two benzoazolyl groups and/or at least one compound containing at least one benzodiazolyl group, as a second screening agent, the said first and second screening agents being present in the subject compositions in proportions eliciting a synergistic effect with regard to the sun protection factors conferred.

The present invention also features the use of the subject compositions in the production of cosmetic compositions suited for the photoprotection of the skin and/or hair against the deleterious effects of ultraviolet radiation, in particular solar radiation.

This invention also features cosmetic regime/regimen for the photoprotection of skin and/or hair against the damaging effects of ultraviolet radiation, in particular solar radiation, which essentially entails topically applying onto the skin/hair a photoprotecting effective amount of a composition in accordance herewith.

DETAILED DESCRIPTION OF BEST MODE AND SPECIFIC/PREFERRED EMBODIMENTS OF THE INVENTION

More particularly according to the present invention, novel cosmetic or dermatological compositions, in particular antisun/sunscreen compositions, are now provided which comprise, formulated into a cosmetically acceptable vehicle, diluent or carrier:

(a) as a first screening agent, at least one benzotriazole compound characteristically having the following structural formula (I):

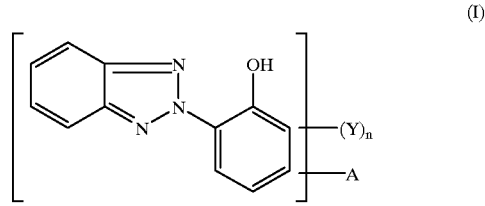

in which A is a hydrogen atom, or a divalent radical —L—W—; the radicals Y, which may be identical or different, are each a $C_1$–$C_{10}$ alkyl radical, a halogen atom, a $C_1$–$C_{10}$ alkoxy radical, or a sulfo group, with the proviso that, in the latter case, two adjacent Y radicals of the same aromatic nucleus can together form an alkylidenedioxy group in which the alkylidene moiety has 1 or 2 carbon atoms, and with the further proviso that the Y radicals are other than a sulfo group when A is other than hydrogen; n has the value 1, 2 or 3; L is a divalent radical of the following formula (II):

$$-(X)_{\overline{m}}-(CH_2)_{\overline{p}}-\underset{Z}{CH}-CH_2- \qquad (II)$$

in which X is O or NH; Z is a hydrogen atom, or a $C_1$–$C_4$ alkyl radical; n is an integer ranging from 0 to 3, inclusive; m is 0 or 1; p is an integer ranging from 1 to 10, inclusive; W is a radical of the following formula (1), (2) or (3):

$$B-\underset{R}{\overset{R}{\underset{|}{Si}}}-O-\left[\underset{R}{\overset{R}{\underset{|}{Si}}}-O\right]_r\left[\underset{R}{\overset{R}{\underset{|}{Si}}}-O\right]_s\underset{R}{\overset{R}{\underset{|}{Si}}}-B \qquad (1)$$

or $$\left[\underset{R}{\overset{R}{\underset{|}{Si}}}-O\right]_t\left[\underset{R}{\overset{R}{\underset{|}{Si}}}-O\right]_u \qquad (2)$$

or $$-Si(R)_3 \qquad (3)$$

in which the radicals R, which may be identical or different, are each a $C_1$–$C_{10}$ alkyl radical, phenyl or a 3,3,3-trifluoropropyl radical, at least 80% by number of the R radicals being methyl; the radicals B, which may be identical or different, are each an R radical, or the V radical of the following formula:

[benzotriazole-phenol structure with substituents $(Y)_n$ and L]

in which Y, n and L are as defined above; r is an integer ranging from 0 to 50, inclusive and s is an integer ranging from 1 to 20, inclusive and, if s=0, at least one of the two B radicals is a radical V; u is an integer ranging from 1 to 6, inclusive and t is an integer ranging from 0 to 10, inclusive, with the proviso that t+u is equal to or greater than 3; and (b) as a second screening agent, at least one compound containing at least two benzoazolyl groups per molecule and/or at least one compound containing, per molecule, at least one benzodiazolyl group.

By the term "containing at least two benzoazolyl groups" are intended, per molecule, at least two groups of the benzoxazolyl, benzothiazolyl or benzimidazolyl type.

By the term "containing at least one benzodiazolyl group" is intended, per molecule, a group of the benzodioxazolyl, benzodithiazolyl or benzodiimidazolyl type.

The benzotriazole compound of formula (I) in accordance with the invention are screening agents already known per se. They are described and prepared according to the syntheses illustrated in U.S. Pat. Nos. 4,316,033 and 4,328,346, EP-B-0,354,145 and EP-B-0,392,883, and EP-B-0,660,701, hereby expressly incorporated by reference.

Exemplary nonsilicone compounds of formula (I) wherein A is a hydrogen atom are:

2-(2'-hydroxy-5'-methylphenyl)benzotriazole (n=1 and Y=$CH_3$), such as the product marketed under the trademark Uvazol P by Enichem Synth or the product marketed under the trademark Tinuvin P by Ciba-Geigy;

2-(2'-hydroxy-3'-butyl-5'-methylphenyl)benzotriazole (n=2 and Y=$CH_3$ and —$C(CH_3)_3$), such as the product marketed under the trademark Uvazol 236 by Enichem Synth;

2-(2'-hydroxy-5'-(t-octyl)phenyl)benzotriazole (n=1 and Y=—$C(CH_3)_2$—$CH_2$—$C(CH_3)_3$), such as the product marketed under the trademark Uvazol 311 by Enichem Synth;

2-(2'-hydroxy-3'-(sec-butyl)-5'-sulfophenyl)-benzotriazole (n=2 and Y=$SO_3H$, Y=—$CH(CH_3)$—$CH_2$—$CH_3$), such as the product marketed under the trademark Cibafast by Ciba-Geigy.

As regards the silicone compounds of formula (I) wherein A is a divalent radical —L—W—, in the definition of the above formulae (1), (2) and (3), the alkyl radicals can be linear or branched and are advantageously selected, in particular, from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred R alkyl radicals according to the invention are the methyl, ethyl, propyl, n-butyl, n-octyl and 2-ethylhexyl radicals. More preferably, the R radicals are all methyl radicals.

As regards the silicone compounds of formula (I) wherein A is a divalent radical —L—W—, it is preferable to formulate those wherein W has the formula (1), namely, linear-chain diorganosiloxanes.

Among the linear diorganosiloxanes according to the present invention, preferred are the statistical derivatives or well-defined block derivatives satisfying at least one and more preferably all of the following conditions:

R is alkyl and more preferably is methyl,

B is alkyl and more preferably is methyl, r ranges from 0 to 15, inclusive; s ranges from 1 to 5, inclusive, n is not zero and preferably is equal to 1 and Y is then methyl, tert-butyl or $C_1$–$C_4$ alkoxy, Z is hydrogen or methyl, m=0 or [m=1 and X=O], p is equal to 1.

As will be seen from the formula (I) above, the linking of the —$(X)_m$—$(CH_2)_p$—$CH(Z)$—$CH_2$— radical to the benzotriazole structural unit, which therefore provides the bonding of said benzotriazole unit to the silicon atom of the silicone chain or backbone (skeleton), can, according to the present invention, take place at any of the available positions presented by the two aromatic nuclei of the benzotriazole:

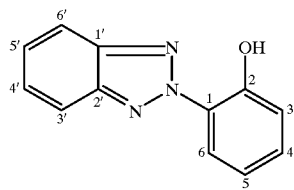

This linking preferably is at the 3-, 4- or 5-position (aromatic nucleus bearing the hydroxyl functional group) or 4'-position (benzene nucleus adjacent to the triazole ring) and more preferably at the 3-, 4- or 5-position. In a preferred embodiment of the invention, the linking takes place at the 3-position.

Likewise, the linking of the Y substituent unit can take place at any of the other positions available in the benzotriazole. However, this linking preferably is at the 3-, 4-, 4'-, 5- and/or 6-position. In a preferred embodiment of the invention, the linking is at the 5-position.

Exemplary compounds which are particularly suitable according to the invention are those having the following structure:

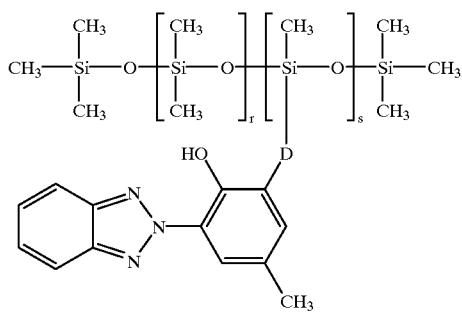

(I')

in which $0 \leq r \leq 15$, preferably $0 \leq r \leq 10$; $1 \leq s \leq 5$, preferably $1 \leq s \leq 3$ and D is the divalent radical:

—(CH$_2$)$_3$— or

—CH$_2$—CH(CH$_3$)—CH$_2$—

In a particularly preferred embodiment of the invention, the benzotriazole silicone has the structural formula (I') in which:

r=0
s=1
D=

—CH$_2$—CH(CH$_3$)—CH$_2$—

In another particularly preferred embodiment of the invention, the benzotriazole silicone has the structural formula (I') in which:

r=0
s=1
D=

—(CH$_2$)$_3$—

The benzotriazole compounds of formula (I) are advantageously formulated in amounts ranging from 0.1% to 15%, preferably from 0.2% to 10%, by weight, with respect to the total weight of the composition; preferably, the overall content of the binary mixture of the first sunscreen (a) and the second sunscreen (b) does not exceed 15% of the total weight of the final composition.

Among the compounds containing at least two benzoazolyl groups in accordance with the invention, preferred are those having the following structural formula (III):

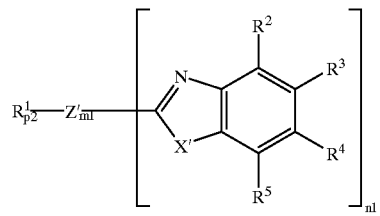

(III)

in which Z' is an organic residue with a valency of $(p_1+n_1)$ comprising one or more double bonds which are positioned such that the double bond completes the system of double bonds of at least two benzoazolyl groups as defined inside the brackets, in order to form a completely conjugated unit; X' is S, O or NR$^6$; R$^1$ is a hydrogen atom, a C$_1$–C$_{18}$ alkyl radical, a C$_1$–C$_4$ alkoxy radical, a C$_5$–C$_{15}$ aryl radical, a C$_2$–C$_{18}$ acyloxy radical, SO$_3$Y' or COOY'; the R$^2$, R$^3$, R$^4$ and R$^5$ radicals, which may be identical or different, are each a nitro group, or a radical R$^1$; R$^6$ is a hydrogen atom, a C$_1$–C$_4$ alkyl radical, or a C$_1$–C$_4$ hydroxyalkyl radical; Y' is a hydrogen atom, Li, Na, K, NH$_4$, 1/2Ca, 1/2Mg, 1/3Al, or a cation resulting from the neutralization of a free acid group by a nitrogenous organic base; $m_1$ is 0 or 1; $n_1$ is a number ranging from 2 to 6; $p_1$ is a number ranging from 1 to 4; with the proviso that $p_1+n_1$ does not exceed the value 6.

The compounds of formula (III) according to the invention are known water-soluble UV-A screening agents described in EP-A-0,669,323. These are described and prepared according to the syntheses illustrated in U.S. Pat. No. 2,463,264 and EP-A-0,669,323, hereby expressly incorporated by reference.

Among the compounds of formula (III) of the invention, preferred are those in which the Z' group is selected from the group consisting of:

(a) an unsaturated linear aliphatic C$_2$–C$_6$ hydrocarbonaceous radical which can be interrupted by a C$_5$–C$_{12}$ aryl radical or a C$_4$–C$_{10}$ heteroaryl radical, such as, for example:

—CH=CH—,

—CH=CH—CH=CH— or

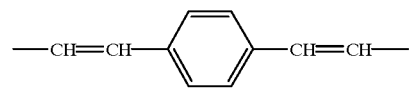

(b) a C$_5$–C$_{15}$ aryl radical which can be interrupted by an unsaturated linear aliphatic C$_2$–C$_6$ hydrocarbonaceous radical, such as, for example, the following radicals:

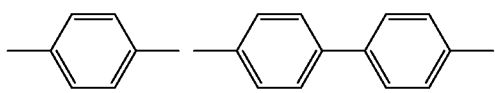

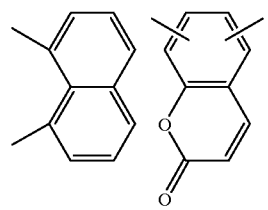

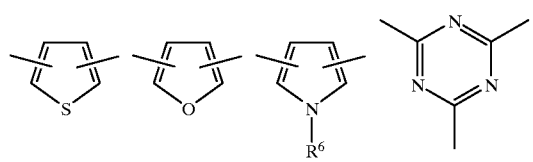

(c) a $C_3$–$C_{10}$ heteroaryl radical, such as, for example, the following groups:

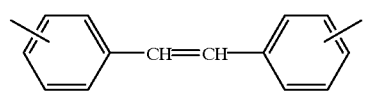

wherein $R^6$ is as defined above, with the proviso that said Z' radicals as described in the paragraphs (a), (b) and (c) may be substituted by $C_1$–$C_6$ alkyl, $C_1$–$C_6$ alkoxy, phenoxy, hydroxyl, methylenedioxy or amino radicals, the amino radicals optionally being substituted by one or two $C_1$–$C_5$ alkyl radicals.

Exemplary compounds of formula (III) are those having the following structural formulae and salts thereof:

Compound 1

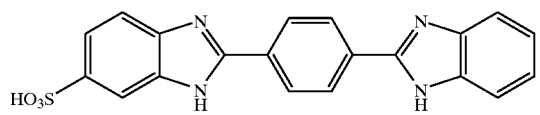

Compound 2

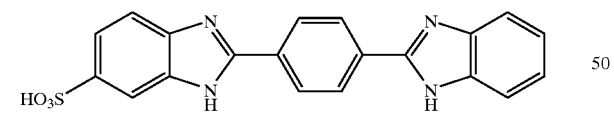

Compound 3

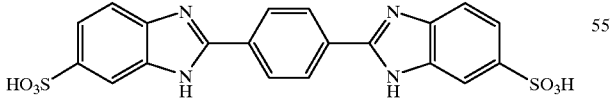

Compound 4

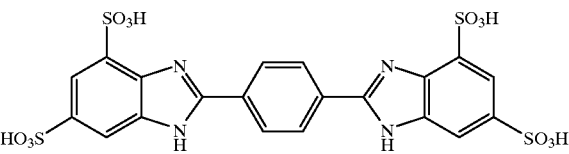

Compound 5

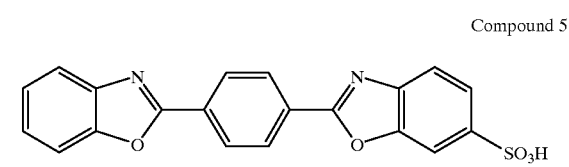

Compound 6

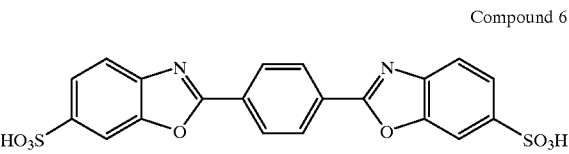

Compound 7

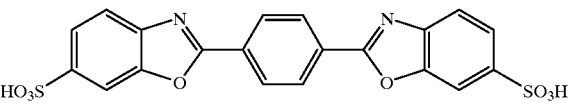

Compound 8

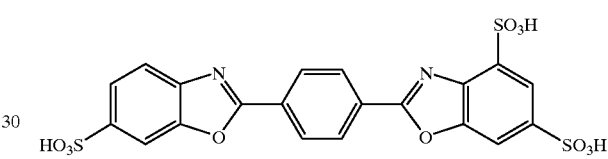

Compound 9

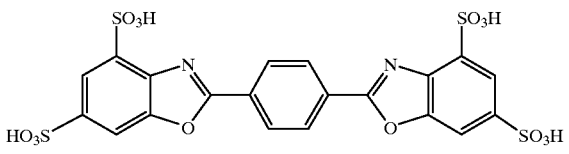

Compound 10

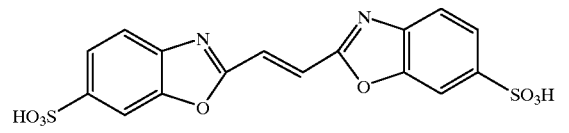

Compound 11

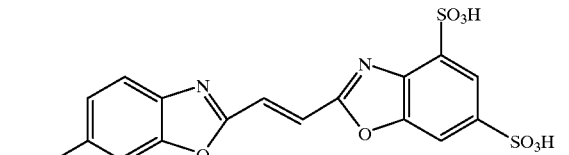

-continued
Compound 12
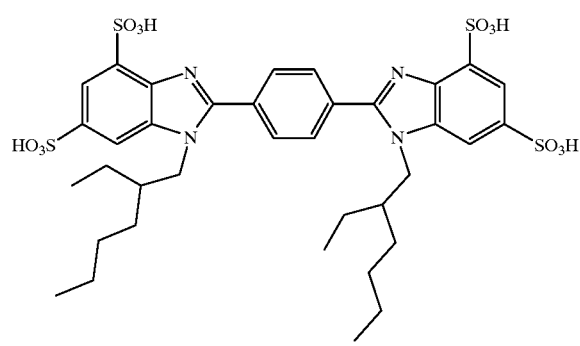
Compound 13
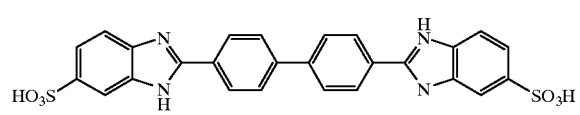
Compound 14
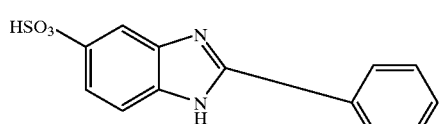
Compound 15
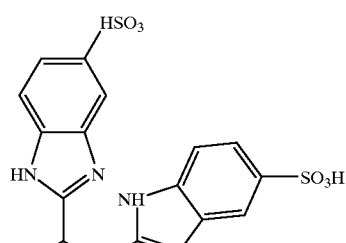
Compound 16
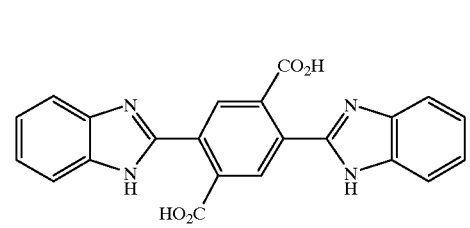
-continued
Compound 17
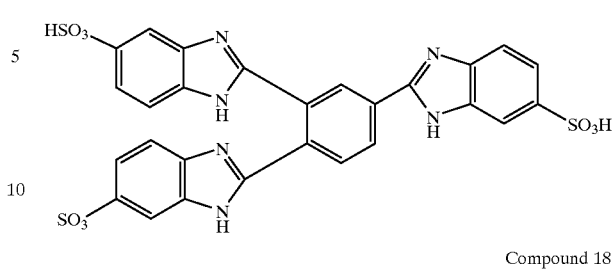
Compound 18
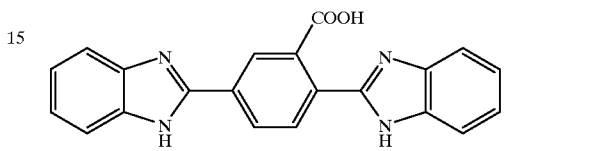
Compound 19
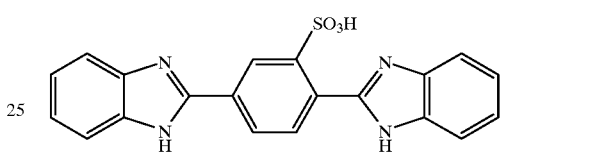
Compound 20
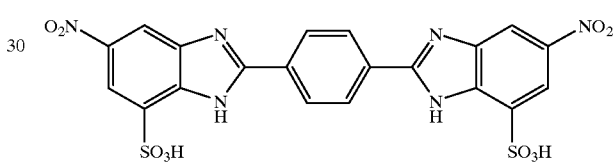
Compound 21
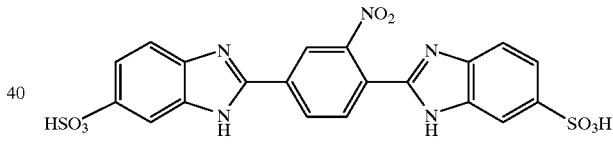
Compound 22
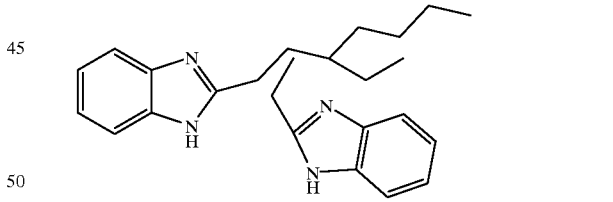
Compound 23
Compound 24
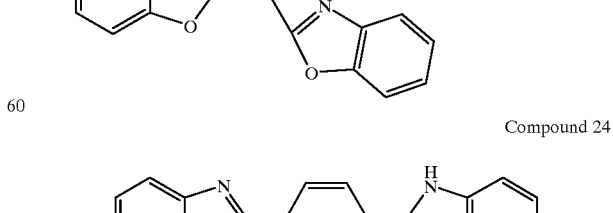

-continued

Compound 25

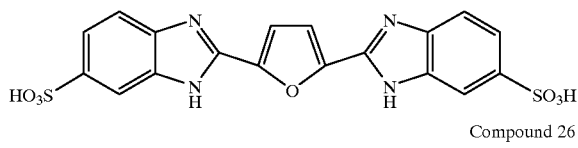

Compound 26

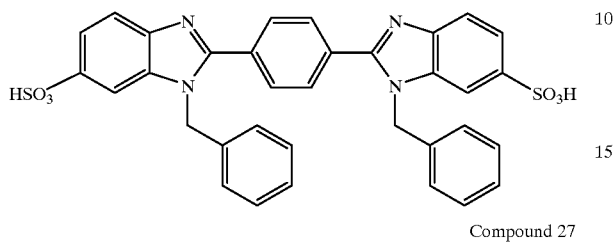

Compound 27

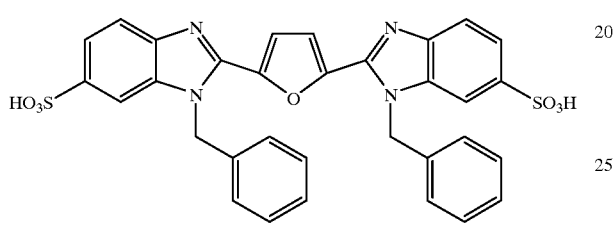

Among these, very particularly preferred are 1,4-bis(benzimidazolyl)-phenylene-3,3',5,5'-tetrasulfonic acid (Compound 4) and its salts having the following structural formula:

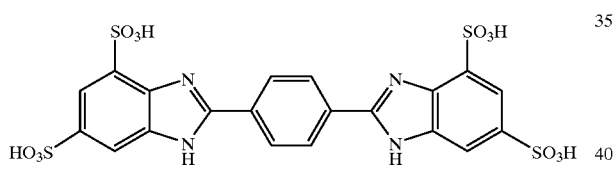

Also exemplary of compounds containing at least two benzoazolyl groups are the following, and salts thereof:

Compound 28

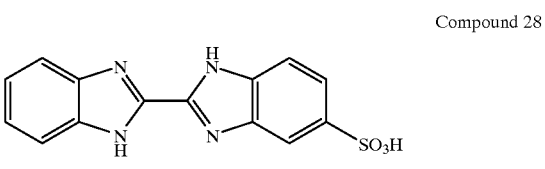

Compound 29

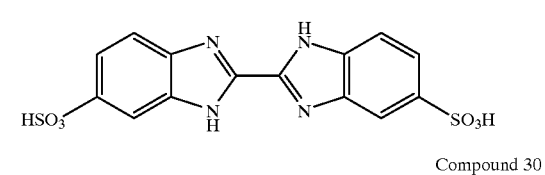

Compound 30

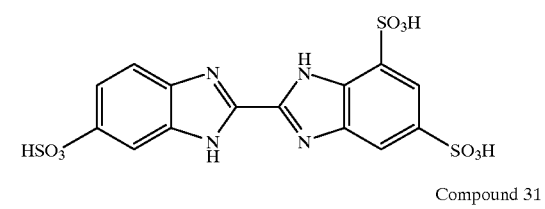

Compound 31

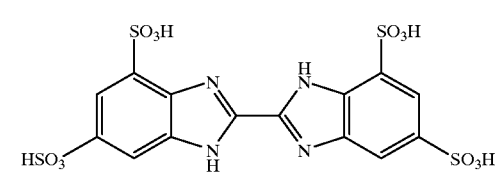

Particularly exemplary of compounds containing at least one benzodiazolyl group according to the invention are the following, and salts thereof:

Compound 32

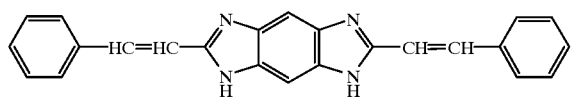

Compound 33

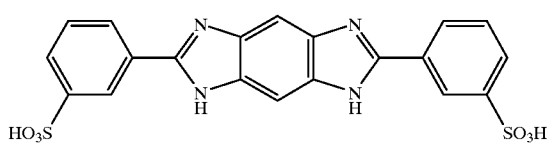

Compound 34

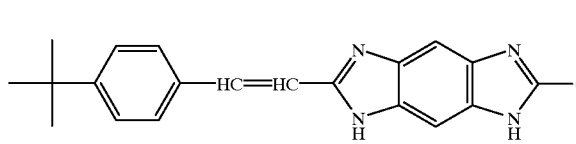

The compound or compounds containing benzoazolyl or benzodiazolyl groups in accordance with the invention are advantageously present in the subject compositions at a concentration ranging from 0.1% to 15%, preferably from 0.2% to 10%, by weight with respect to the total weight of the composition.

As indicated above, in a characteristic embodiment of the present invention, the subject two sunscreens are each present in the final composition in respective proportions such that a substantial and significant synergistic effect is obtained with regard to the protection factor conferred by the resulting combination.

In addition and generally, it should be noted that the concentrations and ratios of the benzotriazole compound of formula (I) and of the compounds containing benzoazolyl or benzodiazolyl groups as described above are selected such that the sun protection factor of the final composition is preferably at least 2.

In another preferred embodiment of the present invention, the cosmetically acceptable medium (vehicle, diluent or carrier) in which the various screening agents are present is an emulsion of oil-in-water type.

The sunscreen/antisun cosmetic compositions according to the invention can, of course, contain one or more additional hydrophilic or lipophilic sunscreens which are active in the UV-A and/or UV-B regions (absorbers), other than the two screening agents indicated above. These additional screening agents are advantageously selected, in particular, from among cinnamic derivatives, salicylic derivatives, camphor derivatives, triazine derivatives, such as those described in EP-863,145, EP-517,104, EP-570,838, EP-796,851, EP-775,698 and EP-878,469, benzophenone derivatives, dibenzoylmethane derivatives, β,β-diphenylacrylate derivatives, benzimidazole derivatives, p-aminobenzoic acid derivatives, or screening polymers and screening silicones, such as those described in WO-93/04665.

Exemplary such additional sunscreens which are active in the UV-A and/or UV-B ranges include:
p-aminobenzoic acid;
oxyethylenated (25 mol) p-aminobenzoate;
2-ethylhexyl p-dimethylaminobenzoate;
N-oxypropylenated ethyl p-aminobenzoate;
glycerol p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl 2-cyano-3,3-diphenylacrylate;
ethyl 2-cyano-3,3-diphenylacrylate;
2-phenylbenzimidazole-5-sulfonic acid and its salts;
3-(4'-trimethylammonio)benzylidenebornan-2-one methyl sulfate;
2-hydroxy-4-methoxybenzophenone;
2-hydroxy-4-methoxybenzophenone-5-sulfonate;
2,4-dihydroxybenzophenone;
2,2',4,4'-tetrahydroxybenzophenone;
2,2'-dihydroxy-4,4'-dimethoxybenzophenone;
2-hydroxy-4-(n-octoxy)benzophenone;
2-hydroxy-4-methoxy-4'-methylbenzophenone;
α-(2-oxoborn-3-ylidene)toluene-4-sulfonic acid and its salts;
3-(4'-sulfobenzylidene)bornan-2-one and its salts;
3-(4'-methylbenzylidene)-d,l-camphor;
3-benzylidene-d,l-camphor;
benzene-1,4-di(3-methylidene-10-camphorsulfonic acid) and its salts;
urocanic acid
2,4,6-tris[p-(2'-ethylhexyl-1'-oxycarbonyl)anilino]-1,3,5-triazine;
2-[p-(tert-butylamido)anilino]-4,6-bis[(p-(2'-ethyl-hexyl-1'-oxycarbonyl)anilino]-1,3,5-triazine;
2,4-bis{[4-(2-ethylhexyloxy)-2-hydroxy]phenyl}-6-(4-methoxyphenyl)-1,3,5-triazine;
the polymer of N-[(2- and 4-)[(2-oxoborn-3-ylidene)-methyl]benzyl]acrylamide;
polyorganosiloxanes comprising a malonate functional group.

The compositions according to the invention can also contain active agents for the artificial tanning and/or browning of the skin (self-tanning agents), such as, for example, dihydroxyacetone (DHA).

The cosmetic compositions according to the invention can also contain pigments or alternatively nanopigments (mean size of the primary particles: generally ranging from 5 nm to 100 nm, preferably from 10 nm to 50 nm) comprising metal oxides which are coated or uncoated, such as, for example, titanium dioxide (amorphous or crystallized in the rutile and/or anatase form), iron oxide, zinc oxide, zirconium oxide or cerium oxide nanopigments which are all UV photoprotective agents well known per se. Furthermore, alumina and/or aluminum stearate are conventional coating agents. Such coated or uncoated metal oxide nanopigments are described, in particular, in EP-A-0,518,772 and EP-A-0,518,773.

The compositions of the invention can additionally contain conventional cosmetic additives and adjuvants selected in particular from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, polymers, propellants, basifying or acidifying agents, dyes, colorants, or any other ingredient commonly formulated into cosmetics, in particular in the production of antisun/sunscreen compositions formulated as emulsions.

Exemplary fatty substances include oils or waxes or their mixtures and they also comprise fatty acids, fatty alcohols and fatty acid esters. The oils are advantageously selected from among animal, vegetable, mineral or synthetic oils and in particular from liquid petrolatum, liquid paraffin, volatile or non-volatile silicone oils, isoparaffins, poly-α-olefins, or fluorinated and perfluorinated oils. Likewise, the waxes are advantageously selected from among animal, fossil, vegetable, mineral or synthetic waxes per se known in this art.

Exemplary organic solvents include the lower alcohols and polyols.

The thickeners are advantegously selected, in particular, from among crosslinked homopolymers of acrylic acid, or modified or unmodified guar gums and celluloses, such as hydroxypropylated guar gum, methylhydroxyethyl-cellulose, hydroxypropylmethyl cellulose or hydroxyethyl-cellulose.

One skilled in this art will of course take care to select this or these optional additional compounds and/or their amounts such that the advantageous properties, in particular the level of photoprotection, intrinsically provided by the binary combination in accordance with the invention are not, or are not substantially, adversely affected by the envisaged addition or additions.

The compositions of the invention are easily formulated according to techniques well known to this art, in particular those suited for the formulation of emulsions of oil-in-water or water-in-oil type.

Such compositions can be provided, in particular, in the form of a simple or complex emulsion (O/W, W/O, O/W/O or W/O/W), such as a cream, a milk, a gel or a cream gel, a lotion, an ointment, a powder or a solid tube or stick and can optionally be packaged as an aerosol and provided in the form of a foam or spray.

When formulated as an emulsion, the aqueous phase thereof can comprise a non-ionic vesicular dispersion prepared according to known techniques (Bangham, Standish and Watkins, *J. Mol. Biol.*, 13, 238 (1965), FR 2,315,991 and FR 2,416,008).

The cosmetic compositions of the invention are useful for protecting the human epidermis or the hair against ultraviolet rays, as an antisun/sunscreen composition or as a makeup product.

When the cosmetic compositions according to the invention are used for the photoprotection of the human epidermis against UV irradiation or as sunscreen compositions, they can be provided in the form of a suspension or dispersion in solvents or fatty substances, in the form of a non-ionic vesicular dispersion, or in the form of an emulsion, preferably of oil-in-water type, such as a cream or a milk, in the form of an ointment, gel, cream gel, powder, solid tube, stick, aerosol foam or spray.

When the cosmetic composition according to the invention are used for the photoprotection of the hair, they can be provided in the form of a shampoo, lotion, gel, emulsion or non-ionic vesicular dispersion and can constitute, for example, a rinse-out composition, to be applied before or after shampooing, before or after dyeing or bleaching and before, during or after permanent-waving or hair straightening, a styling or treating lotion or a styling or treating gel, a lotion or a gel for blow drying or hair setting, or a composition for permanent-waving or straightening, dyeing or bleaching the hair.

When the subject compositions are used as a product for making up the eyelashes, eyebrows or skin, such as a treatment cream for the epidermis, foundation, lipstick, eyeshadow, face powder, mascara or eyeliner, they can be provided in the anhydrous or aqueous, pasty or solid form, such as oil-in-water or water-in-oil emulsions, non-ionic vesicular dispersions, or suspensions.

For example, for the antisun formulations in accordance with the invention which comprise a vehicle of oil-in-water emulsion type, the aqueous phase (comprising in particular the hydrophilic screening agents) generally constitutes from 50% to 95% by weight, preferably from 70% to 90% by weight, with respect to the total weight of the formulation, the oily phase (comprising in particular the lipophilic screening agents) from 5% to 50% by weight, preferably from 10% to 30% by weight, with respect to the total weight of the formulation, and the (co)emulsifier(s) from 0.5% to 20% by weight, preferably from 2% to 10% by weight, with respect to the total weight of the formulation.

As hereinbefore indicated, the present invention also features a regime/regimen for the cosmetic treatment of the skin or hair, to protect these against the deleterious effects of UV radiation, comprising topically applying onto the skin or hair, an effective photoprotective amount of a subject cosmetic composition.

In order to further illustrate the present invention and the advantages thereof, the following specific examples are given, it being understood that same and intended only as illustrative and in nowise limitative.

In said examples to follow, all parts and percentages are given by weight.

The following two (2) compositions according to the invention were formulated via conventional cosmetic technique.

| COMPOSITION | EXAMPLE 1 |
| --- | --- |
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 0.5 g |
| Benzoate of $C_{12}/C_{15}$ alcohols (Witconol TN, Witco) | 10 g |
| Benzotriazole silicone of formula (I') in which: r = 0, s = 1 and $$D = -CH_2-CH(CH_3)-CH_2-$$ | 2.5 g |
| Glycerol | 15 g |
| 1,4-Bis (benzimidazolyl)phenylene-3,3',5,5'-tetrasulfonic acid | 2 g |
| Triethanolamine | q.s. pH 7 |
| Preservatives | q.s. |
| Demineralized water, q.s. for | 100 g |

| COMPOSITION | EXAMPLE 2 |
| --- | --- |
| Glycerol mono/distearate/polyethylene glycol (100 EO) stearate mixture (Arlacel 165 FL, ICI) | 2 g |
| Stearyl alcohol (Lanette 18, Henkel) | 1 g |
| Palm oil stearic acid (Stéarine TP, Stéarinerie Dubois) | 2.5 g |
| Polydimethylsiloxane (Dow Corning 200 Fluid, Dow Corning) | 0.5 g |
| Benzoate of $C_{12}/C_{15}$ alcohols (Witconol TN, Witco) | 12 g |
| Triethanolamine | 0.5 g |
| Benzotriazole silicone of formula (I') in which: r = 0, s = 1 and $$D = -CH_2-CH(CH_3)-CH_2-$$ | 2.5 g |
| Propyleneglycol | 4 g |
| Glycerol | 4 g |
| 1,4-Bis(benzimidazolyl)phenylene-3,3',5,5'-tetrasulphonic acid | 2.5 g |
| Hexadecyl phosphate, potassium salt (Amphisol K, Hoffman-Laroche) | 0.5 g |
| Triethanolamine | q.s. pH 7 |
| Polyacrylic acid (Synthalen K, 3V) | 0.3 g |
| Hydroxypropyl methyl cellulose (Methocel F4M, Dow Chemical) | 0.15 g |
| Preservatives | q.s. |
| Demineralized water, q.s. for | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic suited for the photoprotection of human skin and/or hair, comprising synergistically UV-photoprotecting effective amounts of each of at least one benzotriazole compound having the following structural formula (I):

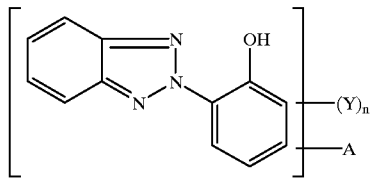
(I)

in which A is a hydrogen atom, or a divalent radical —L—W—; n has the value 1, 2 or 3; the radicals Y, which may be identical or different, are each a $C_1$–$C_{10}$ alkyl radical, a halogen atom, a $C_1$–$C_{10}$ alkoxy radical or a sulfo groups, with the proviso that, in the latter case, two adjacent Y radicals of the same aromatic nucleus can together form an alkylidenedioxy group in which the alkylidene moiety has 1 on 2 carbon atoms, with the further proviso that the Y radicals are other than a sulfo group when A is other than hydrogen; L is a divalent radical of the following formula (II):

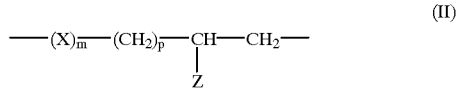
(II)

in which X is O or NH; Z is a hydrogen atom, or a $C_1$–$C_4$ alkyl radical; n is an integer ranging from 0 to 3, inclusive; m is 0 or 1; p is an integer ranging from 1 to 10, inclusive; W is a radical having the following formula (1), (2) or (3):

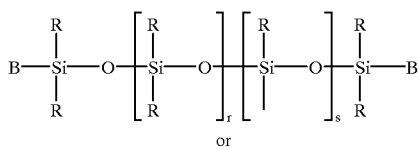
(1)

or

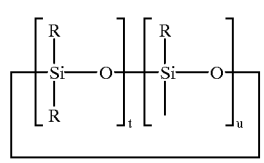
(2)

or

(3)

in which formulae the radicals R, which may be or different, are each a $C_1$–$C_{10}$ alkyl radical, phenyl or 3,3,3-trifluoropropyl radical, at least 80% by number of the R radicals being methyl; the radicals B, which may be identical or different, are each an R radical or a V radical having the following formula:

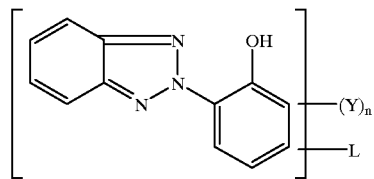

in which Y, n and L are as defined above; r is an integer ranging from 0 to 50, inclusive, and s is an integer ranging from 1 to 20, inclusive and, if s=0, at least one of the two B radicals os a radical V; u is an integer ranging from 1 to 6, inclusive, and t is an integer ranging from 0 to 10, inclusive, with the proviso that t+u is equal to or greater than 3; and (b) at least one compound containing at least two benzoazolyl groups per molecule and/or at least one compound containing, per molecule, at least one benzodiazolyl group, formulated into a topically applicable, cosmetically acceptable vehicle, diluent or carrier therefor.

2. The sunscreen/cosmetic composition as defined by claim 1, said at least one compound of formula (I) comprising-2-(2'-hydroxy-5'-methylphenyl)benzotriazole; -2-(2'-hydroxy-3'-butyl-5'-methylphenyl)benzotriazole; -2-(2'-hydroxy-5'-(t-octyl)phenyl)benzotriazole; or -2-(2'-hydroxy-3'-(sec-butyl)-5'-sulphophenyl)-benzotriazole.

3. The sunscreen/cosmetic composition as defined by claim 1, said at least one benzotriazole compound of formula (I) comprising one in which A is a divalent radial —L—W— and W has the structure of formula (1) wherein at least one of the following conditions is satisfied:

R is alkyl;

r ranges from 0 to 15, inclusive; s ranges from 1 to 5 inclusive;

n is not zero and Y is methyl, tert-butyl or $C_1$–$C_4$ alkoxy;

Z is hydrogen or methyl;

m=0 or [m=1 and X=O];

p is equal to 1.

4. The sunscreen/cosmetic as defined by claim 3, wherein the said benzotriazole compound of formula (I) all of said conditions are satisfied.

5. The sunscreen/cosmetic composition as defined by claim 1, said at least one benzotriazole compound having the structural formula (I'):

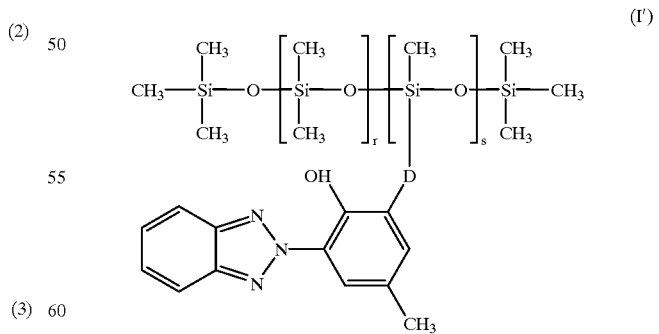
(I')

in which $0 \leq 1 \leq 15$; $1 \leq s \leq 5$; and D is the divalent

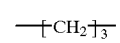

-continued or $$-CH_2-\underset{\underset{CH_3}{|}}{CH}-CH_2-.$$

6. The sunscreen/cosmetic composition as defined by claim 5, said at least one benzotriazole compound having the structural formula (I') in which
r==0; s=1; and D=

$$-CH_2-\underset{\underset{CH_3}{|}}{CH}-CH_2-.$$

7. The sunscreen/cosmetic as defined by claim 5, said at least one benzotriazole compound having the structural formula (I') in which
r=0; s=1; and D=

$$-(CH_2)_3-.$$

8. The sunscreen/cosmetic composition as defined by claim 1, comprising from 0.1% to 15% by weight of said at least one benzotriazole compound of formula (I).

9. The sunscreen/cosmetic composition as defined by claim 8, comprising from 0.2% to 10% by weight of said at least one benzotriazole compound of formula (I).

10. The sunscreen/cosmetic composition as defined by claim 1, comprising at least one compound containing and having the following structural formula (III):

$$\left[ R^1_{p2}-Z'_{m1} \underset{X'}{\overset{N}{\underset{\|}{\bigg\langle}}} \begin{array}{c} R^2 \\ R^3 \\ R^4 \\ R^5 \end{array} \right]_{n1} \quad (III)$$

in which Z' is an organic residue with a valency of $(p_1+n_1)$ comprising one or more double bonds which are positioned such that the double bond completes the system of double bonds of at least two benzoazolyl groups as defined inside the brackets, in order to form a completely conjugated unit; X' is S, O or $NR^6$; $R^1$ is a hydrogen atom, a $C_1-C_{18}$ alkyl radical, a $C_1-C_4$ alkoxy radical, a $C_5-C_{15}$ aryl radical, a $C_2-C_{18}$ acyloxy radical, $SO_3Y'$ or $COOY'$; the $R^2$, $R^3$, $R^4$ and $R^5$ radicals, which may be identical or different, are each a nitro group or a radical $R^1$; $R_6$ is a hydrogen atom, a $C_1-C_4$ alkyl radical or a $C_1-C_4$ hydroxyalkyl radical; Y, is a hydrogen atom, Li, Na, K, $NH_4$, 1/2Ca, 1/2Mg, 1/3Al, or a cation resulting from the neutralization of a free acid group by a nitrogenous organic base; $m_1$ is 0 or 1; $n_1$ is a number ranging from 2 to 6; $p_1$ is a number ranging from 1 to 4; with the proviso that $p_1+n_1$ does not exceed the value 6.

11. The sunscreen/cosmetic composition as defined by claim 10, wherein formula (III) Z' is (a) an unsaturated linear aliphatic $C_2-C_6$ hydrocarbonaceous radical which can be interrupted by a $C_5-C_{12}$ aryl group or a $C_4-C_{10}$ heteroaryl; (b) a $C_5-C_{15}$ aryl group which can be interrupted by an unsaturated linear aliphatic $C_2-C_6$ hydrocarbonaceous radical; or (c) a $C_3-C_{10}$ heteroaryl group, with the proviso that said Z' radical may be substituted by $C_1-C_6$ alkyl, $C_1-C_6$ alkoxy, phenoxy, hydroxyl, methylenedioxy or amino radicals, the amino radicals optionally being substituted by one or 2 $C_1-C_5$ alkyl radicals.

12. The sunscreen/cosmetic composition as defined by claim 10, wherein formula (III) the Z' radical is selected from among the following:

$-CH=CH-$ $-CH=CH-CH=CH-$ $-CH=CH-\phantom{x}\text{(phenyl)}\phantom{x}-CH=CH-$ (biphenyl and terphenyl structures)

(naphthalene and coumarin structures)

$-\text{(phenyl)}-CH=CH-\text{(phenyl)}-$ (thiophene, furan, pyrrole with $R^6$, and triazine structures)

13. The sunscreen/cosmetic composition as defined by claim 10, said at least one compound of formula (III) being selected from among the following compounds, or salts thereof:

Compound 1

(bis-benzimidazole with $HO_3S$ substituent)

Compound 2

(bis-benzimidazole with $HO_3S$ and $SO_3H$ substituents)

Compound 3

(bis-benzimidazole with two $SO_3H$ substituents)

Compound 4
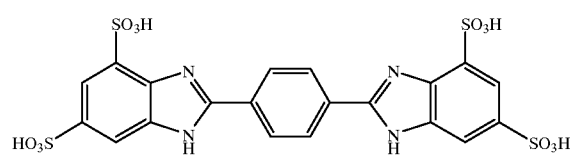
Compound 5
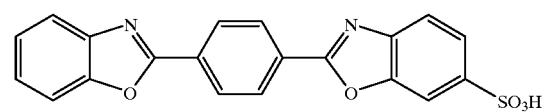
Compound 6
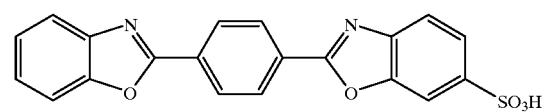
Compound 7
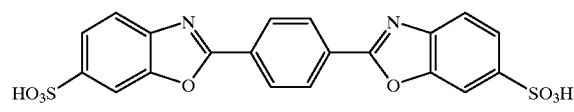
Compound 8
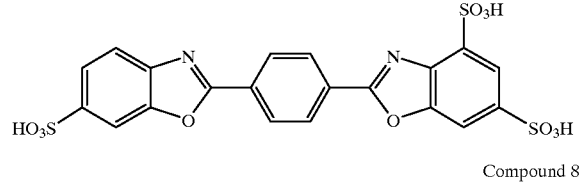
Compound 9
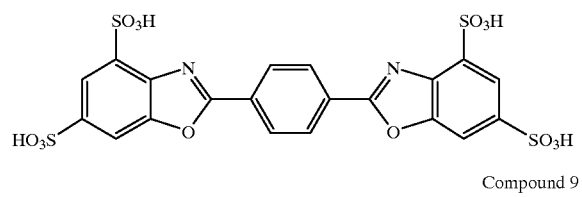
Compound 10
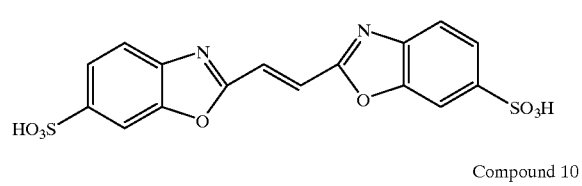
Compound 11
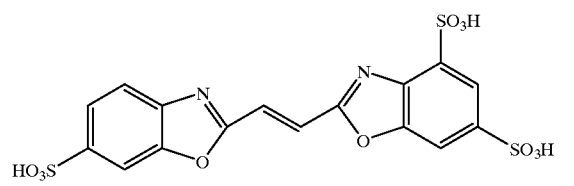
Compound 12
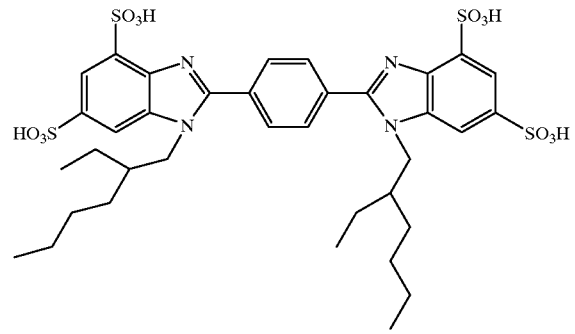
Compound 13
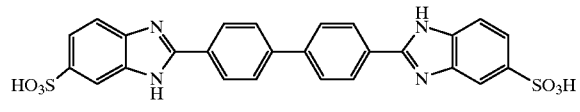
Compound 14
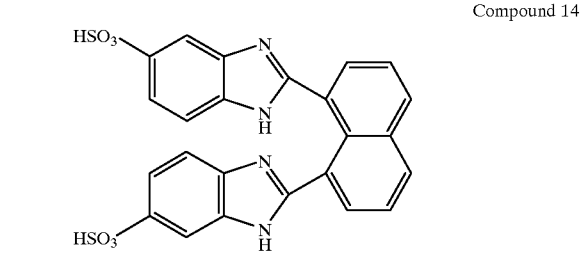
Compound 15
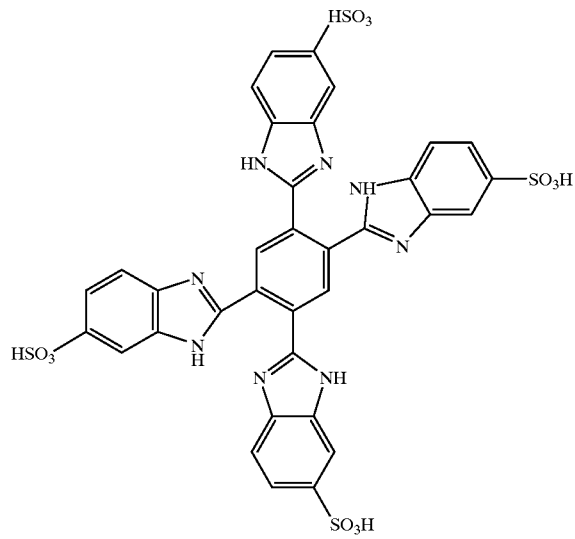
Compound 16
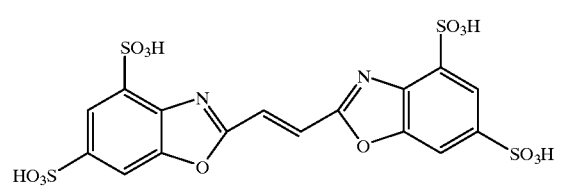

Compound 17

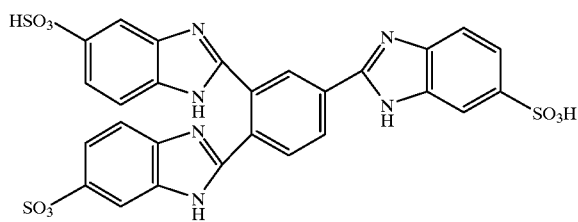

Compound 18

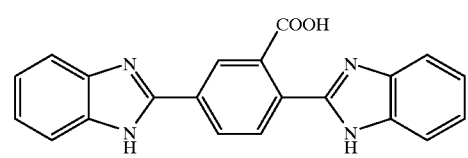

Compound 19

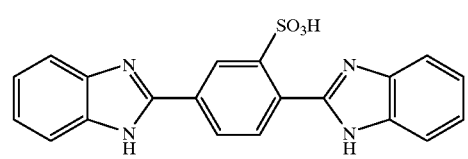

Compound 20

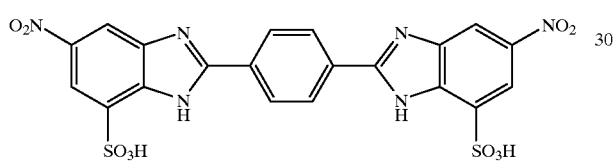

Compound 21

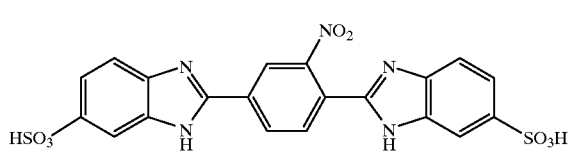

Compound 22

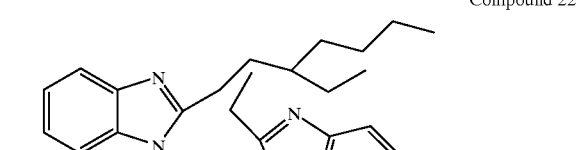

Compound 23

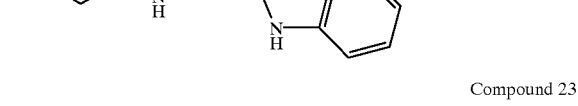

Compound 24

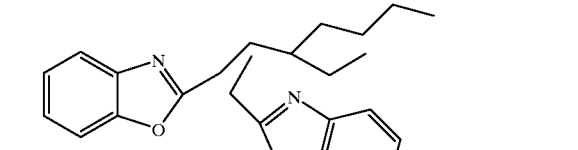

Compound 25

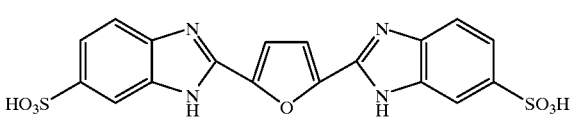

Compound 26

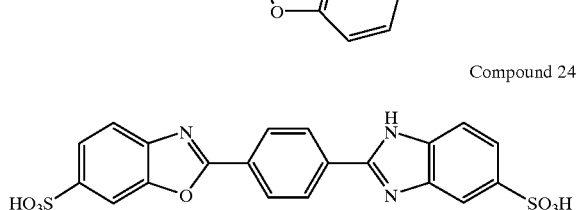

Compound 27

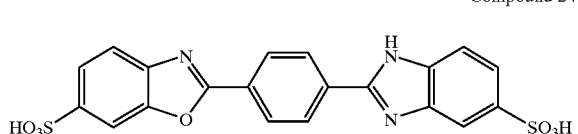

14. The sunscreen/cosmetic composition as defined by claim 10, said at least one compound of formula (III) comprising 1,4-bis(benzimidazolyl)phenylene-3,3',5,5'-tetra-sulfonic acid (Compound 4) having the following structural formula, or salt thereof:

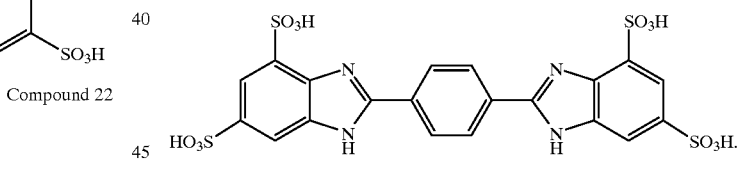

15. The sunscreen/cosmetic composition as defined by claim 1, comprising at least one compound containing at least two benzoazolyl groups selected from among the following compounds, or salts thereof:

Compound 28

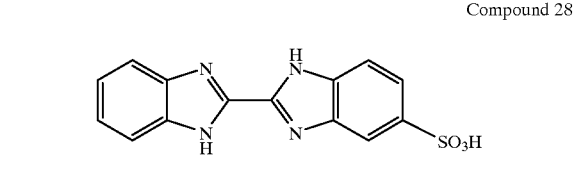

Compound 29

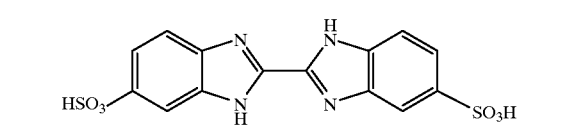

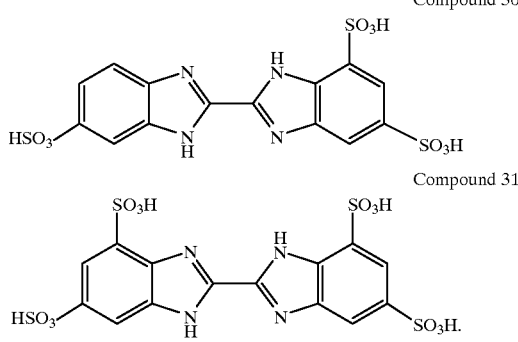

Compound 30

Compound 31

16. The sunscreen/cosmetic composition as defined by claim 1, comprising at least one compound containing at least one benzodiazolyl group selected from among the following compounds, or salts thereof:

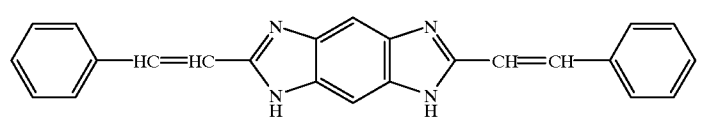

Compound 32

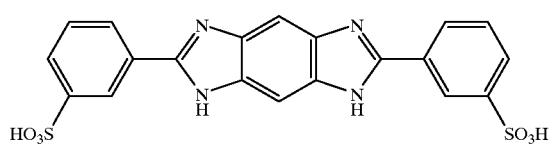

Compound 33

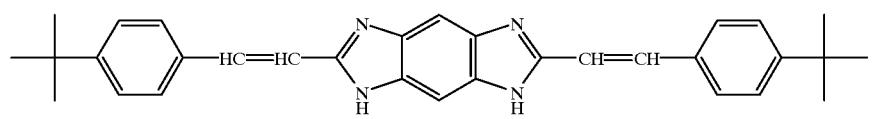

Compound 34

17. The sunscreen/cosmetic composition as defined by claim 1, comprising from 0.1% to 15% by weight to of said at least one compound containing benzoazolyl and/or benzodiazolyl groups.

18. The sunscreen/cosmetic composition as defined by claim 17, comprising from 0.2% to 10% by weight to of said at least one compound containing benzoazolyl and/or benzodiazolyl groups.

19. The sunscreen/cosmetic composition as defined by claim 1, formulated as an oil-in-water emulsion.

20. The sunscreen/cosmetic composition as defined by claim 1, formulated as a water-in-oil emulsion.

21. The sunscreen/cosmetic composition as defined by claim 1, further comprising at least one additional hydrophilic or lipophilic organic UV-A and/or UV-B sunscreen.

22. The sunscreen/cosmetic composition as defined by claim 21, further comprising at least one cinnamic derivative, salicylic derivative, camphor derivative, triazine derivative, benzophenone derivative, debenzoylmethane derivative, benzimidazole derivative, α,β-diphenylacrylate derivative, p-aminobenzoic acid derivative, sunscreen polymer, or sunscreen silicone.

23. The sunscreen/cosmetic composition as defined by claim 1, further comprising a photoprotective effective amount of particulates of at least one coated or uncoated inorganic pigment or nanopigment.

24. The sunscreen/cosmetic composition as defined by claim 23, said at least one pigment or nanopigment comprising titanium dioxide, zinc oxide, iron oxide, zirconium oxide, cerium oxide, or mixture thereof.

25. The sunscreen/cosmetic composition as defined by claim 1, further comprising at least one active agent for the artificial tanning and/or browning of human skin.

26. The sunscreen/cosmetic composition as defined by claim 1, further comprising at least one cosmetically acceptable adjuvant or additive.

27. The sunscreen/cosmetic composition as defined by claim 26, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

28. The sunscreen/cosmetic composition as defined by claim 1, comprising a nonionic vesicle dispersion, emulsion, cream, milk, gel, cream gel, ointment, suspension, dispersion, powder, solid stick or tube, foam or spray.

29. The sunscreen/cosmetic composition as defined by claim 1, comprising a makeup.

30. The sunscreen/cosmetic composition as defined by claim 29, comprising an anhydrous or aqueous solid or paste, emulsion, suspension, or dispersion.

31. The sunscreen/cosmetic composition as defined by claim 1, comprising a shampoo, lotion, gel, nonionic vesicle dispersion, hair lacquer, or rinse.

32. The sunscreen/cosmetic composition as defined by claim 1, having a sun protection factor of at least 2.

33. A regime/regimen for protecting human skin and/or hair against the deleterious effects of ultraviolet irradiation, comprising topically applying thereto an effective amount of the sunscreen/cosmetic composition as defined by claim 1.

34. A regime/regimen for protecting human skin and/or hair against the deleterious effects of solar radiation, comprising topically applying thereto an effective amount of the sunscreen/cosmetic composition as defined by claim 1.

\* \* \* \* \*